(12) United States Patent
Ladewski (10) Patent No.: US 6,208,412 B1
(45) Date of Patent: Mar. 27, 2001

(54) METHOD AND APPARATUS FOR DETERMINING OPTICAL QUALITY

(75) Inventor: Theodore B. Ladewski, Ann Arbor, MI (US)

(73) Assignee: Visteon Global Technologies, Inc., Dearborn, MI (US)

(*) Notice: Subject to any disclaimer, the term of this patent is extended or adjusted under 35 U.S.C. 154(b) by 0 days.

(21) Appl. No.: 09/332,236

(22) Filed: Jun. 14, 1999

(51) Int. Cl.[7] .................................................. G01N 21/88

(52) U.S. Cl. ........................................ 356/239.1; 356/124

(58) Field of Search .............................. 356/239.1, 239.2, 356/124, 124.5

(56) References Cited

U.S. PATENT DOCUMENTS

| | | |
|---|---|---|
| 4,076,426 | 2/1978 | Gross et al. . |
| 4,255,055 | 3/1981 | Schave . |
| 4,285,745 | 8/1981 | Farabaugh . |
| 4,291,990 | 9/1981 | Takasu . |
| 4,461,570 | 7/1984 | Task et al. . |
| 4,591,998 * | 5/1986 | Kuperman et al. ................. 364/521 |
| 4,647,197 | 3/1987 | Kitaya et al. . |
| 4,653,909 * | 3/1987 | Kuperman ......................... 356/124.5 |
| 4,742,237 | 5/1988 | Ozawa . |
| 4,776,692 | 10/1988 | Kalawsky . |
| 4,802,759 | 2/1989 | Matsumoto et al. . |
| 4,832,451 * | 5/1989 | Trescott .............................. 356/124 |
| 4,866,287 | 9/1989 | Weber . |
| 4,895,448 | 1/1990 | Laird . |
| 5,003,187 | 3/1991 | Zumbrunn et al. . |
| 5,076,698 | 12/1991 | Smith et al. . |
| 5,128,550 * | 7/1992 | Erbeck .............................. 356/374 |
| 5,135,308 | 8/1992 | Kuchel . |
| 5,135,309 | 8/1992 | Kuchel et al. . |
| 5,146,293 | 9/1992 | Mercer et al. . |
| 5,175,601 | 12/1992 | Fitts . |
| 5,216,481 * | 6/1993 | Minato ............................... 356/240 |
| 5,225,890 | 7/1993 | Lee et al. . |
| 5,307,151 | 4/1994 | Hof et al. . |
| 5,309,222 | 5/1994 | Kamei et al. . |
| 5,311,286 | 5/1994 | Pike . |
| 5,315,384 | 5/1994 | Heffington et al. . |
| 5,319,445 | 6/1994 | Fitts . |
| 5,343,288 | 8/1994 | Cohen et al. . |
| 5,343,294 | 8/1994 | Kuchel et al. . |

(List continued on next page.)

FOREIGN PATENT DOCUMENTS

| | | |
|---|---|---|
| 44 15 834 A1 | 11/1995 | (DE) . |
| 0 769 674 A2 | 4/1997 | (EP) . |
| 8-328150 | 12/1996 | (JP) . |
| WO 96/12160 | 4/1996 | (WO) . |

OTHER PUBLICATIONS

"Shearing Interferometer With Scanned Photodiode Array And Microcomputer For Automatic Transparency Distortion Measurements", by J. Taboada et al, SPIE vol. 153, Advances in Optical Metrology (1978), pp. 139–145.

"Interferometer For Measurement Of The Wedge And Lens Power Of Flat Glass And Laminates", by B.N. Dereck, Plastics Products Research, Parkersburg, WV, May 2, 1978, pp. 1–7, plus attachments.

"Novel Three Dimensional Computer Vision Techniques With Applications To Deformation Measurement, 3–D Shape Gauging And Surface Quality Inspection", by Shouhong Tang, 1991, pp. 1–169.

(List continued on next page.)

Primary Examiner—Richard A. Rosenberger
(74) Attorney, Agent, or Firm—Larry I. Shelton (57) ABSTRACT

A method of determining optical quality of a transparent product includes passing a first gray-scale pattern through the material; obtaining a first image of the first pattern with an image pickup device after the first pattern has passed through the material; and determining optical quality of the material based on data obtained from the first image. An apparatus for determining optical quality of such a material is also disclosed.

25 Claims, 4 Drawing Sheets

U.S. PATENT DOCUMENTS

| | | |
|---|---|---|
| 5,367,378 | 11/1994 | Harding et al. . |
| 5,452,079 | 9/1995 | Okugawa . |
| 5,471,297 | 11/1995 | Tani . |
| 5,471,307 | 11/1995 | Koliopoulos et al. . |
| 5,568,258 | 10/1996 | Uemura et al. . |
| 5,581,352 | 12/1996 | Zeien . |
| 5,612,786 | 3/1997 | Huber et al. . |
| 5,636,025 | 6/1997 | Bieman et al. . |
| 5,646,733 | 7/1997 | Bieman . |
| 5,691,784 | 11/1997 | Hausler et al. . |
| 5,691,811 | 11/1997 | Kihira . |
| 5,694,479 | 12/1997 | Guering et al. . |
| 6,100,990 | 8/2000 | Ladewski . |

OTHER PUBLICATIONS

"Laboratory Apparatus For The Optical Distortion Measurement In Automotive Windows", Budgetary Data Sheet, Two Sampesl of Computer Screen and Schematic Layout of Tai–Tecnolgia Automazione Innovazione—S.p.A., 1994, Rome, Italy.

"A Human Factors Analysis Of Optical Distortion For Automotive Windshields", by Minoru Makiguchi et al, SAE Technical Paper No. 940390, dated Feb. 1994, pp. 47–57.

"A New Automatic Optical Distortion Measuring System For Automotive Windshields", by Shigeyuki Seto et al, SAE Technical Paper No. 940391, dated Feb. 1994, pp. 59–64.

"Novel Optical Techniques For Window Glass Inspection", by M. Savolainen et al, Meas. Sci. Technol. 6, ©1995 IPO Publishing Ltd., pp. 1016–1021.

"WaveScope—WaveScope™ wavefront Sensor Ssytem WFS–01, Table Top Optical Wavefront Sensor", Technical Bulletin of Adaptive Optics Associates, Inc., Cambridge, Massachusetts, 1997, 2 pages.

"Distortiometer Ssytem SD–1900—Digital Image Analysis System For Measuring Optical Distortion In Automotive Transparencies", Strainoptic Technologies Inc., North Wales, PA, Apr. 1997, 10 pages.

"Automatic On–Line Quality Control—Raw Glass Defects and Optical Quality Monitoring, FloatScan 'Cather'& 'Optics'", technical brochure of Grenzebach Corporation, Newnan, GA, Jul. 21, 1997, pp. 1–9.

"Inspection Of Float Glass Using A Novel Retro–Reflective Laser Scanning System", by Jonathan D. Holmes, Optical Scanning Systems: Design And Applications, SPIE vol. 3131, Jul. 30–31, 1997, San Diego, CA, pp. 180–190.

"Eliminating Optical Quality Headaches", Quality Control, Glass International, Sep. 1997, pp. 57, 59.

"LASOR" Technical Bulletin of Laser Sorter GmbH, Oct. 20, 1997, one page.

"Technical Support Package On Technique For Measuring Optical Quality of a Window", by David I. Brown et al, Feb. 1998, NASA Tech. Brief, vol. 22, No. 2, Item #109, 8 pages.

SAE Technical Bulletin No. 980917, "Measuring Curvature Of Mirrors Using Image Analysis", by Dorothy J. Helder, Feb. 24, 1998, pp. 147–152.

"Holographic Optics And Machine Vision Inspection Systems For Flat Glass, Tubing & Pressed Ware", technical bulletin of TAI Incorporated, Chantilly, VA, undated, 4 pages.

"Ombroligne OM90", technical bulletin of Lasor Laser Sorter GmbH, Germany, undated, 1 page.

"Windshield Optical Distortion Analyzer", technical brochure of R&D Reflections Inc. Wayne, Ohio, undated, 2 pages.

* cited by examiner

METHOD AND APPARATUS FOR DETERMINING OPTICAL QUALITY

TECHNICAL FIELD

The invention relates to an apparatus and method for determining optical quality of a transparent product, wherein the apparatus and method involve passing one or more gray-scale patterns through the product.

BACKGROUND OF THE INVENTION

A prior method for determining optical quality of a transparent product, such as a front windshield for a motor vehicle, involves projecting an array of dots through the product and onto a screen. The dots are then measured manually, and the measurements are compared with predetermined, standard measurements to evaluate optical distortion of the product.

Because the dots are measured manually, this method is rather time-consuming, fatiguing and error prone. Furthermore, the method provides limited coverage of the product. For example, distortion occurring between dots is not detected.

Another method for determining optical quality of a transparent product involves using a test pattern comprising a plurality of diamonds or equivalent pattern. A moveable light source is positioned behind the test pattern, and its movement is synchronized with a moveable line-scan camera positioned in front of the test pattern. As the light source and camera move with respect to the product, the camera views images of the test pattern as seen through the product. Measurements of diamonds detected in the images are compared with undistorted diamonds to evaluate distortion of the product. This method also provides limited coverage of the product. Furthermore, the apparatus used to practice the method is relatively slow, complex and costly.

DISCLOSURE OF INVENTION

The invention overcomes the shortcomings of the prior art by providing a method and apparatus for determining optical quality of a transparent product at any and all points on the product. Furthermore, the method and apparatus provide accurate and repeatable results.

Under the invention, a method of determining optical quality of a transparent product includes passing a first gray-scale pattern through the product; obtaining a first image of the first pattern with an image pickup device after the first pattern has passed through the product; and determining optical quality of the product based on data obtained from the first image.

Exemplary gray-scale patterns that may be used to practice the method include sinusoidal gratings as well as sawtooth gratings. Advantageously, the gray-scale patterns may be projected through the product, or generated behind the product. Consequently, the method may be used with a variety of product and apparatus configurations.

More specifically, the method includes determining a phase for each of a plurality of pixels of the first image, wherein each pixel corresponds to a particular point on the product. One or more optical characteristics are then determined for each of a plurality of points on the product based on the phase at the corresponding pixel.

An apparatus according to the invention for determining optical quality of a transparent product includes an image generating device for generating a gray-scale pattern such that the gray-scale pattern may be passed through the product. The apparatus further includes an image pickup device for obtaining an image of the gray-scale pattern after the pattern has passed through the product, and an image analyzing device in communication with the image pickup device. The image analyzing device includes instructions for determining optical quality of the product based on the image of the gray-scale pattern.

These and other objects, features and advantages of the invention are readily apparent from the following detailed description of the best modes for carrying out the invention when taken in conjunction with the accompanying drawings.

BEST MODES FOR CARRYING OUT THE INVENTION

Figure 1:
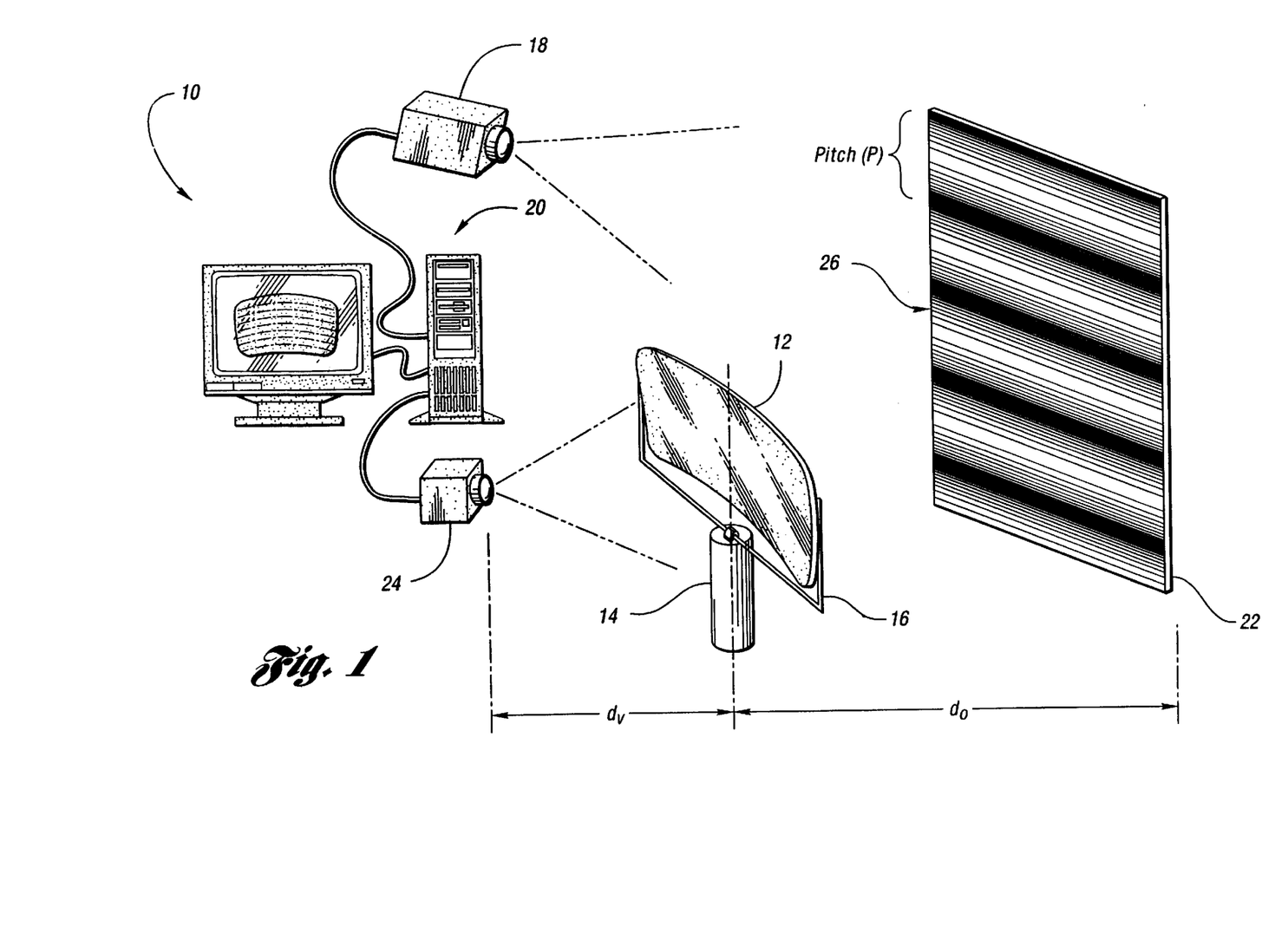
FIG. 1 is a schematic view of an apparatus for practicing a method according to the invention for determining optical quality of a transparent product such as a motor vehicle windshield, wherein the apparatus includes a projector for projecting a sequence of phase-shifted sinusoidal gratings onto a screen, and a camera for obtaining images of the gratings as seen through the windshield.

FIG. 1 shows an apparatus 10 according to the invention for determining optical quality of a transparent product such as a front windshield 12 for a motor vehicle. Other exemplary transparent products include magnifying glasses, eyeglasses, aircraft windshields, windows, and fluids having various indices of refraction. The windshield 12 is held in a predetermined position and angle of inclination on a rotatable work table 14 by means of a holder 16.

As shown in FIG. 1, the apparatus 10 includes a projector 18 in communication with a computer 20. The projector 18 is used to project one or more gray-scale targets or patterns onto a reference plane, such as a screen 22, which is located behind the windshield 12 at a distance $d_o$ from the windshield 12. Gray-scale pattern as used herein refers to a pattern having a varying light intensity or color profile, such as a sinusoidal grating or a sawtooth grating, wherein each point in the pattern has a well defined phase. Advantageously, the projector 18 and computer 20 can be used to quickly generate and project a sequence of phase-shifted gray-scale patterns onto the screen 22. Alternatively, the apparatus 10 may include any suitable image generating device for providing one or more gray-scale patterns, such as a computer monitor, television monitor, painted pattern, or slide projector.

The apparatus 10 further includes an image pickup device, such as a digital camera 24, for obtaining digital images of the gray-scale patterns. Preferably, the camera 24 is disposed in front of the windshield 12 at a distance $d_v$ from the windshield 12, as shown in FIG. 1, so as to obtain digital images of the gray-scale patterns as seen through the windshield 12. The camera 24 is also in communication with the computer 20, and the camera 24 transmits signals to the computer 20 corresponding to the digital images. The computer 20 is used to process the signals so as to determine optical quality of the windshield 12 as explained below in greater detail.

A method according to the invention for determining optical quality of the windshield 12 involves determining one or more optical parameters or characteristics of the windshield 12 at discrete locations or points on the windshield 12. The optical characteristics are determined based on phase changes introduced to one or more gray-scale patterns by the windshield 12, as a result of the patterns passing through the windshield 12. In order to calculate such characteristics, wrapped vertical and horizontal phase distributions of images of the one or more gray scale patterns are first determined. As used herein, vertical and horizontal phase distributions refer to vertical and horizontal phase values, respectively, at a plurality of pixels of the images. The phase distributions may be determined using any one of several known techniques.

If the windshield 12 is stationary, a phase-shift technique is preferably utilized. Under the phase-shift technique, in order to determine the vertical phase distribution introduced by the windshield 12, the projector 18 first projects a horizontally oriented gray-scale pattern, such as a first grating 26 of horizontal lines having a sinusoidal intensity profile and a pitch p, onto the screen 22. The camera 24 then detects or otherwise obtains an image of the first grating 26 as seen through the windshield 12, and the camera 24 transfers the image to the computer 20 where the image is stored.

Next, the computer 20 shifts the first grating 26 vertically by a distance p/n to create a second, phase-shifted grating (not shown), where n is the desired number of phase-shifted gratings to be utilized in determining the vertical phase distribution. Furthermore, n should be greater than or equal to 3, and is preferably 4. The projector 18 then projects the second, phase-shifted grating onto the screen 22. Next, the camera 24 obtains an image of the second, phase-shifted grating as seen through the windshield 12, and transfers the image to the computer 20 where the image is stored.

This process is continued until n images have been obtained by the camera 24, and transferred to the computer 20. Thus, the phase-shift technique involves generating a sequence of n phase-shifted gray-scale patterns, and obtaining images of each pattern within the sequence as seen through the windshield 12. Furthermore, each image comprises a plurality of pixels, and each pixel corresponds to a particular point on the windshield 12.

Figure 2:
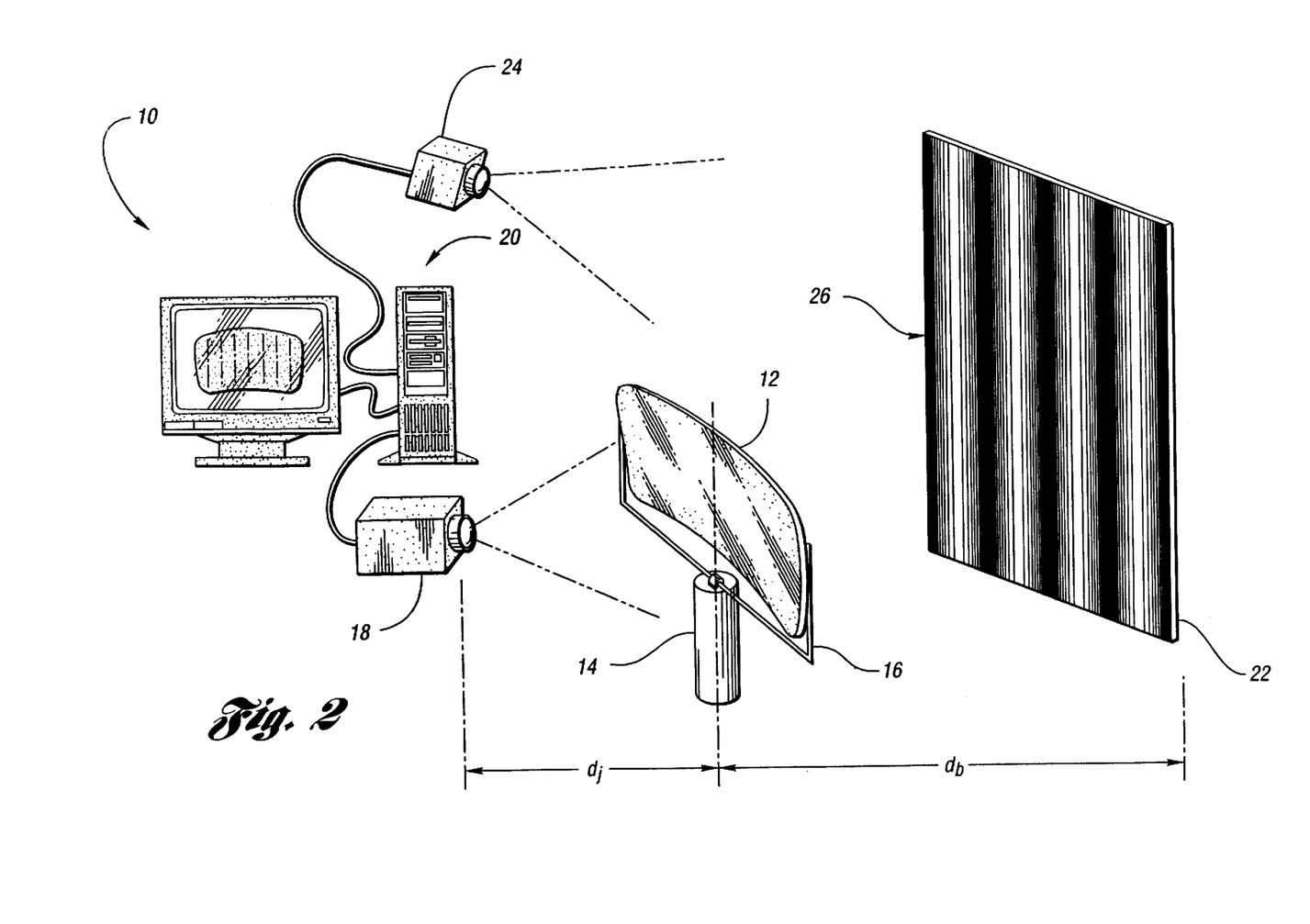
FIG. 2 is a schematic view of an alternative configuration of the apparatus, wherein the projector is positioned so as to project the sequence of phase-shifted sinusoidal gratings through the windshield and onto the screen, and the camera is positioned so as to obtain images of the gratings as seen on the screen.

Because this technique involves obtaining images of the patterns as seen through the windshield 12, it may be referred to as a view-through approach. is Alternatively, as shown in FIG. 2, the phase-shift technique may involve projecting a sequence of phase-shifted gray-scale patterns through the windshield 12 and onto the screen 22 or other reference plane, and obtaining images of the patterns as seen on the screen 22. This alternative approach may be referred to as a project-through approach. Generally, then, the method involves passing one or more gray-scale patterns through the windshield 12, wherein such a description covers both view-through and project-through approaches.

Next, the computer 20 analyzes the n images to determine vertical phase $\phi^y$ for each of the pixels of the images. The vertical phase $\phi_y$ for each pixel is determined based on light intensities at the same pixel location on the n different images, and the general equation for determining $\phi_y$ for a particular pixel (x,y) is as follows:

$$\varphi(x, y) = \tan^{-1}\left[-\frac{\sum_{i=0}^{n-1} I_{i+1}(x, y)\sin\frac{2\pi i}{n}}{\sum_{i=0}^{n-1} I_{i+1}(x, y)\cos\frac{2\pi i}{n}}\right],$$

where $I_i(x,y)$=light intensity at pixel (x,y) of image i. For n=4, the equation becomes:

$\phi_y(x,y)$=arctan$((I_4(x,y)-I_2(x,y))/(I_1(x,y)-I_3(x,y)))$.

The above process is then repeated using vertically oriented gray-scale patterns, such as a grating of vertical lines having a sinusoidal intensity and a known pitch, to determine horizontal phase $\phi_x$ for each of the pixels of the images.

If the windshield 12 is moving, then a Fourier transform technique is preferably utilized to determine the phase distributions. Under the Fourier transform technique, only one horizontally oriented gray-scale pattern and one vertically oriented gray-scale pattern are required to determine the vertical phase and horizontal phase, respectively, for each of the pixels. Briefly, the technique involves obtaining an image of each pattern, and performing a Fourier transform of each image. Next, each Fourier transform is edited, and an inverse Fourier transform is performed to determine the vertical and horizontal phases for each pixel. Additional details regarding the Fourier transform technique may be found in "Fourier-Transform Method of Fringe-Pattern Analysis for Computer-Based Topography and Interferometry," by M, Takeda, H. Ina, and S. Kobayashi, which is hereby incorporated by reference.

Figure 3:
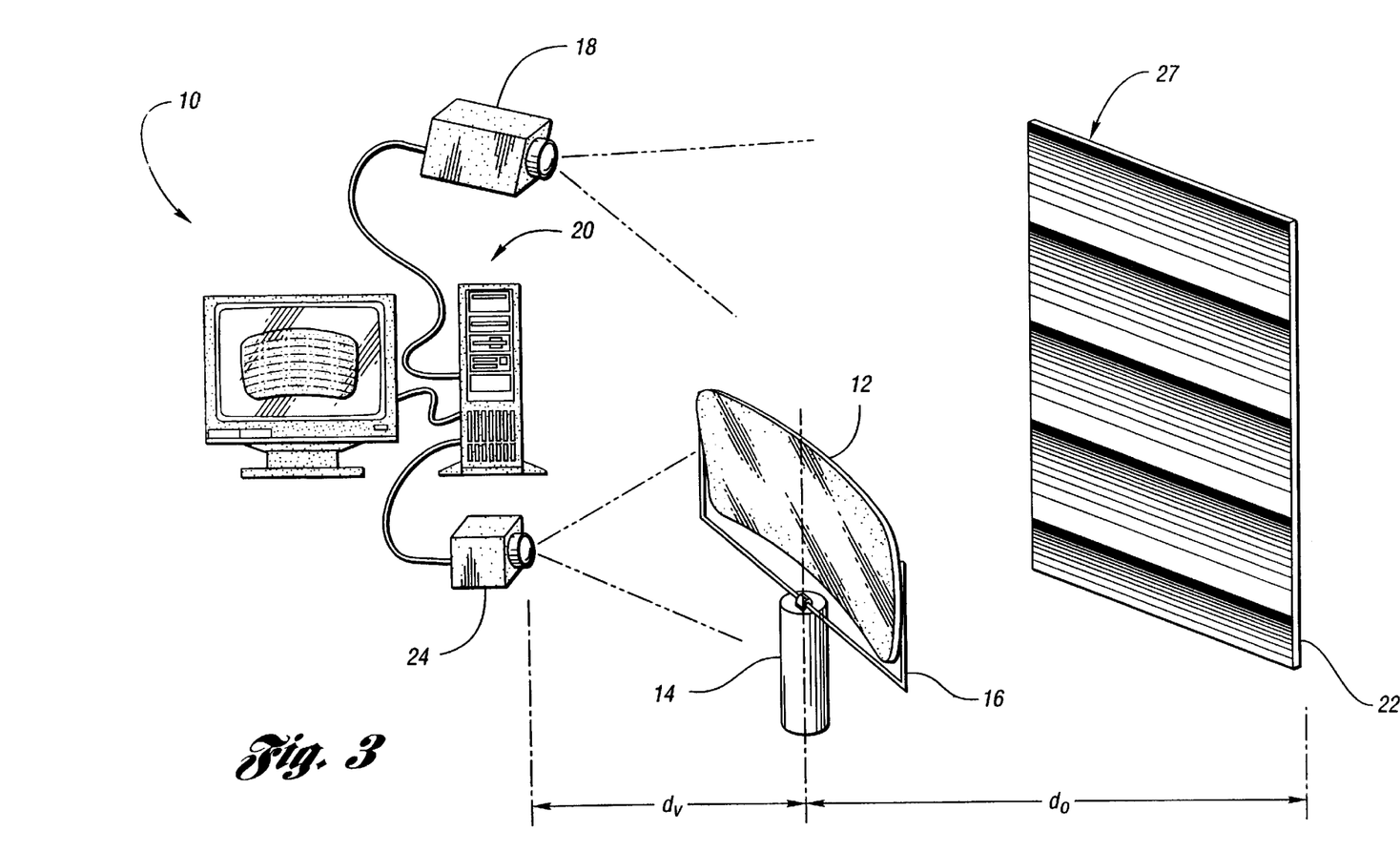
FIG. 3 is a schematic view of the apparatus having a similar configuration as in FIG. 1, and showing the projector projecting a sawtooth grating onto the screen.

If the camera 24 or other image pickup device has linear intensity response, and if the intensity profiles generated by the projector 18 or other image generating device are relatively accurate, then a technique that involves generating sawtooth gratings is preferably utilized to determine the phase distributions. Under this technique, as shown in FIG. 3, the projector 18 generates a horizontally oriented sawtooth grating 27 on the screen 22. The camera 24 then obtains an image of the sawtooth grating 27 as seen through the windshield 12, and the computer 20 acquires the image to determine a light intensity value I at each pixel (x,y).

Next, the projector 18 generates a uniformly white target on the screen 22, the camera 24 obtains an image of the white target, and the computer 20 acquires the image to determine a maximum light intensity value $I_{max}$ at each pixel (x,y). The projector 18 then generates a uniformly dark target on the screen 22, the camera 24 obtains an image of the dark target, and the computer 20 acquires the image to determine a minimum light intensity value $I_{min}$ at each pixel (x,y).

Next, the computer 20 determines the vertical phase $\phi_y$ at each pixel (x,y) using the following equation:

$y(x,y)=2\pi(I(x,y)-I_{min}(x,y))/(I_{max}(x,y)-I_{min}(x,y))$

A second phase-shifted and/or inverted horizontally oriented sawtooth grating may be required to fill in the phase distribution where the light intensity changes rapidly.

The above process is then repeated using one or more vertically oriented sawtooth gratings to determine horizontal phase $\phi_x$ for each of the pixels of the corresponding image. Because this technique requires determination of only three variables for each pixel, phase distributions can be determined relatively quickly.

Alternatively, any other suitable technique for determining the phase distributions may be utilized, such as a phase synchronization technique, a demodulation-convolution technique, a 3-point Fourier fit, or a polynomial fit fringe order technique. Furthermore, any of the techniques may involve view-through or project-through approaches.

After the vertical and horizontal phase distributions have been determined, the computer 20 then determines the partial derivatives of the vertical and horizontal phases for each pixel. The partial derivatives of the vertical phase for a particular pixel (x,y) may be determined using the following equations:

$$\frac{\partial \varphi_y}{\partial x}(x, y) = \varphi_y(x+1, y) - \varphi_y(x, y) + k\pi, \text{ and}$$

$$\frac{\partial \varphi_y}{\partial y}(x, y) = \varphi_y(x, y+1) - \varphi_y(x, y) + k\pi,$$

where k=−1, 0, or +1 as needed to correct for the $2\pi$ ambiguity in the wrapped phase. Similarly, the partial derivatives of the horizontal phase for a particular pixel (x,y) may be determined using the following equations:

$$\frac{\partial \varphi_x}{\partial x}(x, y) = \varphi_x(x+1, y) - \varphi_x(x, y) + k\pi, \text{ and}$$

$$\frac{\partial \varphi_x}{\partial y}(x, y) = \varphi_x(x, y+1) - \varphi_x(x, y) + k\pi.$$

Next, optical characteristics are determined for each point on the windshield 12 by determining the optical characteristics at each corresponding pixel of the image or images based on the phase data obtained at each pixel. For example, instantaneous apparent vertical magnification $m_y$ and instantaneous apparent horizontal magnification $m_x$ may be determined at each pixel (x,y) using the following equations:

$$m_y(x, y) = \rho_y(x, y) / \frac{\partial \varphi_y}{\partial y}(x, y), \text{ and}$$

$$m_x(x, y) = \rho_x(x, y) / \frac{\partial \varphi_x}{\partial x}(x, y),$$

where $\rho_y(x,y)$ and $\rho_x(x,y)$ are the vertical reference phase gradient and horizontal reference phase gradient, respectively, at a particular point (x,y). As used herein, reference phase gradient at a pixel (x,y) refers to the rate of phase change at pixel (x,y) when apparent magnification is 1.0. In other words, reference phase gradient is the rate of phase change at a particular pixel of an undistorted image. Furthermore, $\rho_y$ and $\rho_x$ are represented by the following equations:

$$\rho_y(x, y) = \frac{\partial \varphi_{yo}}{\partial y}(x, y) = \varphi_{yo}(x, y+1) - \varphi_{yo}(x, y) + k\pi \text{ and}$$

$$\rho_x(x, y) = \frac{\partial \varphi_{xo}}{\partial x}(x, y) = \varphi_{xo}(x+1, y) - \varphi_{xo}(x, y) + k\pi,$$

where $\phi_{y0}(x,y)$ and $\phi_{x0}(x,y)$ are the vertical and horizontal phases, respectively, without the windshield 12 positioned in the apparatus 10.

The derivation of the above equations regarding instantaneous apparent magnification will now be explained. Generally, apparent magnification $m_a$ for a typical lens is defined as the ratio of the angle subtended by the image of an object, which is referred to as image angle, to the angle subtended by the object, which is referred to as object angle. For lenses with varying apparent magnification values, instantaneous apparent magnification m in a direction $\omega_0$ is defined as the ratio of the change of image angle to object angle, and is represented by the following equation:

$$m(\omega_o) = \lim_{\Delta\omega > 0} \Delta\omega_i / \Delta\omega_o = d\omega_i / d\omega_o,$$

where $\Delta\omega_i$ is the subtended image angle, and $\Delta\omega_o$ is the subtended object angle.

Figure 4:
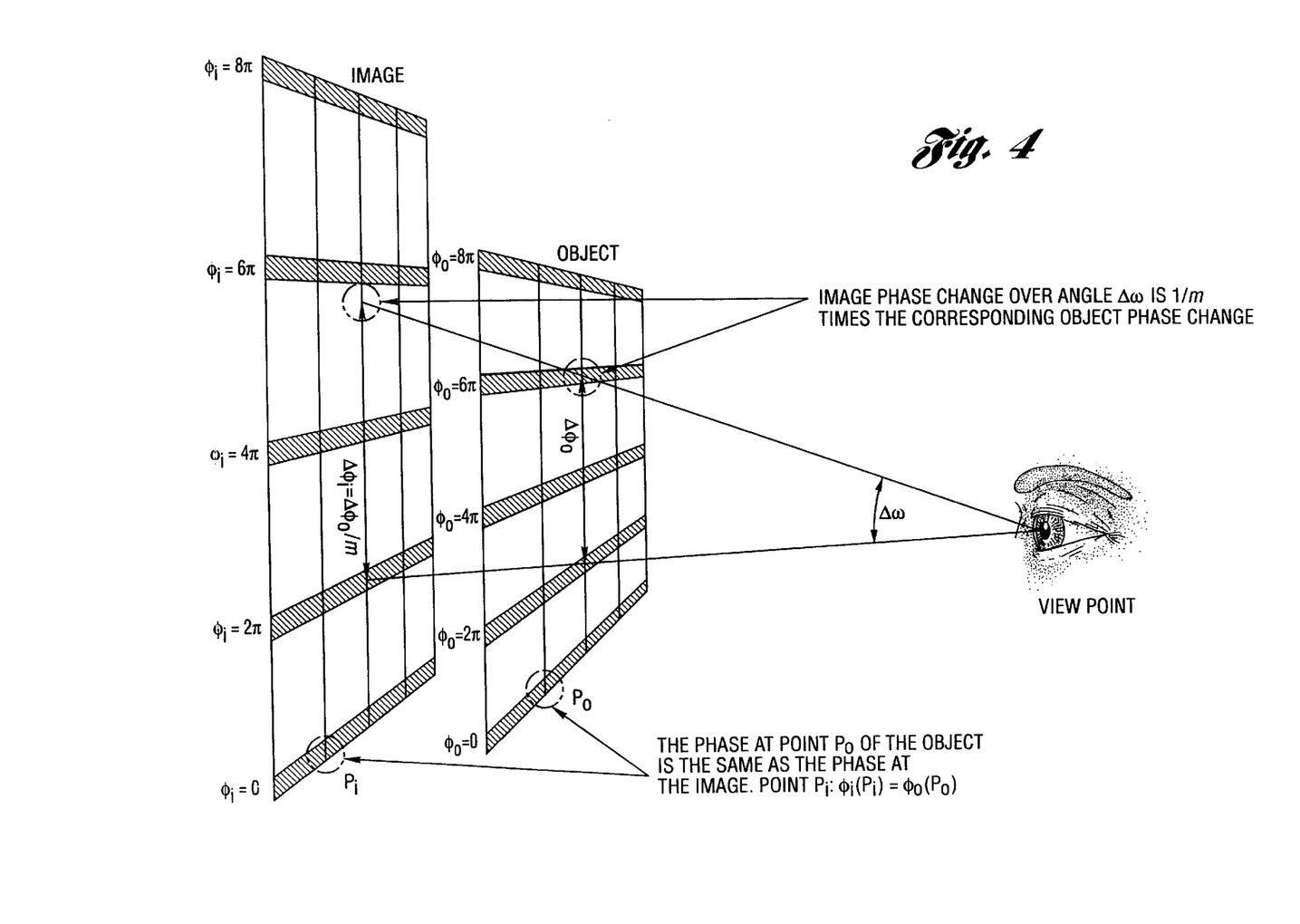
FIG. 4 a schematic view of an object having a periodic structure, and an image of the object.

In the case where the object has a periodic structure, as shown in FIG. 4, such that each object point has a well defined phase, then each image point will have a phase identical with the phase at the corresponding object point. For example, the phase at a particular image point $P_i$ is identical to the phase at the corresponding object point $P_o$. Because $d\omega_i/dy_i = d\omega_o/dy_o$, the equation for m then becomes:

$$m = (d\phi_o/dy_o)/(d\phi_i/dy_i)$$

Thus, to determine magnification at a particular point on a lens, the reference phase gradient is divided by the phase gradient as influenced by the lens.

Focal length $f$ at each pixel may also be determined in the x and y directions. Based on the thin lens formula and triangle relationships, the relationship between the instantaneous apparent magnification m and the focal length $f$ for a view-through approach is:

$$1/m = 1 - l/((1/d_o + 1/d_v)f)$$

where $d_o$ is the distance from the windshield 12 to the screen 22, and $d_v$ is the distance from the windshield 12 to the view point, such as the camera 24. Given the above expression for m, the effective vertical focal length $f_y$ and the effective horizontal focal length $f_x$ may be determined at each pixel (x,y) from the following equations:

$$f_y(x, y) = \left(\frac{1}{(1/d_o + 1/d_v)(1 - 1/m_y(x, y))}\right), \text{ and}$$

$$f_x(x, y) = \left(\frac{1}{(1/d_o + 1/d_v)(1 - 1/m_x(x, y))}\right).$$

For these equations to be valid, the focal length $f$ must satisfy one of the two following conditions: either $f \leq 0$, or $f > 1/(1/d_o + 1/d_v)$. If $f > 1(1/d_o + 1/d_v)$, then the windshield 12 functions as a positive lens and forms a real image. In this case, the camera 24 must be between the windshield 12 and the real image.

Additionally, lens power or optical power OP may be determined at each pixel (x,y) in the x and y directions using the following equations:

$$OP_y(x,y) = 1/f_y(x,y) = (1/d_o + 1/d_v)(1/m_y(x,y)), \text{ and}$$

$$OP_x(x,y) = 1/f_x(x,y) = (1/d_o + 1/d_v)(1/m_x(x,y))$$

where $f_y$ and $f_x$ are the effective vertical or horizontal focal lengths, respectively, and $m_y$ and m, are the instantaneous apparent magnifications in the corresponding directions.

For a project-through approach as shown in FIG. 2, the relationship between the instantaneous apparent magnification m and the focal length $f$ is:

$$m = [(d_j + d_b)f - d_f d_b]/(d_j f),$$

where $d_j$ is the distance from the windshield 12 to the projector 18, and $d_b$ is the distance from the windshield 12 to the screen 22. Focal length and optical power in the x and y directions may then be determined using this relationship.

In order to evaluate optical distortion perceived by a human observer, such as a vehicle occupant, it is helpful to have an optical measure that accounts for the distance the occupant will be from the windshield 12 during use. One such optical measure is standardized apparent magnification $m_s$, which may be used to evaluate lens effects as perceived by the occupant when looking at an object at infinity while located a standard distance $d_s$ from the windshield 12. Using the above equations involving instantaneous apparent magnification m and focal length $f$, the standardized apparent magnification $m_s$ may be expressed as:

$$m_s = \left(-1\frac{1}{(1/d_s + 1/\infty)f}\right)^{-1} = \frac{1}{1-(d_s/d_o + d_s/d_v)(1-1/m)},$$

where m and $f$ are determined in the x or y directions, as necessary, using the procedure described above in detail. With this equation, standardized apparent magnification $m_s$ may be determined in the x and y directions at each pixel.

Another aspect of the invention involves evaluating astigmatic characteristics of the windshield 12. If the instantaneous apparent magnification m for a particular point (x,y) is not the same in all directions, then the windshield 12 is astigmatic at point (x,y). In such a case, point (x,y) will have a maximum instantaneous apparent magnification a in a certain direction θ, and a minimum instantaneous apparent magnification b in a direction perpendicular to θ, where θ is referred to as cylinder axis angle.

Discrete phase differences may be used to determine maximum and minimum instantaneous apparent magnifications a and b, as well as cylinder angle θ for each point on the windshield 12. The discrete phase differences are expressed by the following equations:

$$\Delta_y\phi_y = \phi_y(x,y+1) - \phi_y(x,y) = [(ac^2+bs^2)/ab]\rho_y,$$

$$\Delta_y\phi_x = \phi_x(x,y+1) - (x,y) = [-cs(a-b)/ab]\rho_x,$$

$$\Delta_x\phi_x = \phi_x(x+1,y) - \phi_x(x,y) = [(as^2+bc^2)/ab]\rho_x, \text{ and}$$

$$\Delta_x\phi_y = \phi_y(x+1, y) - \phi_y(x,y) = [-cs(a-b)ab]\rho_y,$$

where $c=\cos(\theta)$, $s=\sin(\theta)$, $\Delta_y\phi^y$ is the vertical difference in vertical phase $\phi_y$, $\Delta_y\phi_x$ is the vertical difference in horizontal phase $\phi_x$, $\Delta_x\phi_x$ is the horizontal difference in horizontal phase $\phi_x$, and $\Delta_x\phi_y$ is the horizontal difference in vertical phase $\phi_y$. These equations reduce to the following:

$$S = \Delta_y\phi_y/\rho_y + \Delta_x\phi_x/\rho_x = 1/a + 1/b;$$

$$C = \Delta_x\phi_x\rho_x - \Delta_y\phi_y/\rho_y = [1/a - 1/b] \cos(2\theta);$$

$$D = -[4(\Delta_x\phi_y/\rho_y)(\Delta_y\phi_x/\rho_x) + C^2]^{1/2} = 1/a - 1/b;$$

$$a = 2/(S+D); \quad b = 2/(S-D)$$

$$\theta = 0.5 \arctan[(\Delta_y\phi_x/\rho_x + \Delta_x\phi_y/\rho_y)C]; \text{ and}$$

$$\epsilon = \Delta_x\rho_y - \Delta_y\phi_x;$$

where ε is a consistency check. If a, b and θ are constant within one pixel of pixel (x,y), and the light intensity measurements are made without error, then ε will be 0. Result validity can be checked by examining ε at each point (x,y), and calculations voided where ε exceeds a selected threshold. Optical characteristics such as focal length, optical power and standardized apparent magnification may then be determined for each pixel using the maximum and minimum instantaneous apparent magnifications a and b, and the above equations.

Vertical disparity may also be evaluated for the windshield 12. Vertical disparity, experienced by an observer looking at an object at infinity, is the difference in altitude angle between the direction to the image of the object as seen from the left eye of the observer, and the direction to the image of the object as seen from the right eye. In order to calculate vertical disparity, the wrapped vertical phase distribution must be unwrapped using one of several known algorithms to obtain the unwrapped vertical phase $\Phi_y$ at each pixel. Next, the vertical disparity $\psi_e$ is determined for each pixel (x,y) using the following equation:

$$\psi_e(x,y) = \arctan([p(\Phi_y(x,y) - \Phi_y(x+x_e,y))/2\pi]/d_o,$$

where $d_o$ is the distance from the windshield 12 to the screen 22, $x_e$ is the horizontal distance corresponding to the interocular spacing projected to the windshield 12, and p is the pitch of the particular gray-scale pattern.

Next, the optical characteristics for each point on the windshield 12 may be evaluated to determine whether the optical quality of the windshield 12 is acceptable. For example, the optical characteristics for each point may be compared with predetermined, acceptable values. As another example, the computer 20 may generate one or more output images or profiles that graphically represent optical characteristics of the windshield 12. Furthermore, such images or profiles may be color coded so that potential problem areas of the windshield 12 may be easily identified.

Advantageously, by utilizing gray-scale patterns rather than black and white patterns known as binary patterns, the apparatus and method enable optical characteristics to be determined at all points on the windshield 12. Consequently, the apparatus and method of the invention provide a significantly more complete determination of optical quality of the windshield 12 compared with prior art apparatuses and methods. Because the optical characteristics of the windshield 12 are determined by the computer 20, the invention also provides an efficient and accurate determination of optical quality of the windshield 12. Furthermore, because the method preferably includes determining standardized apparent magnification, optical performance of the windshield 12 in use conditions may be effectively predicted.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of determining optical quality of a transparent product, the method comprising:
   passing a first gray-scale pattern through the product;
   obtaining a first image of the first pattern with an image pickup device after the first pattern has passed through the product; and
   determining apparent magnification for each of a plurality of points on the product based on data obtained from the first image.

2. The method of claim 1 wherein passing a first gray-scale pattern comprises projecting the first gray-scale pattern through the product.

3. The method of claim 1 wherein passing a first gray-scale pattern comprises passing a first sinusoidal grating through the product.

4. The method of claim 1 wherein passing a first gray-scale pattern comprises passing a first sawtooth grating through the product.

5. The method of claim 1 further comprising:
   passing a second gray-scale pattern through the product wherein the second pattern is shifted with respect to the first pattern by a predetermined phase; and obtaining a second image of the second pattern with an image pickup device after the second pattern has passed through the product;

wherein determining apparent magnification for each of a plurality of points of the product further includes determining apparent magnification for each point based on data obtained from the second image.

6. The method of claim 1 further comprising determining a phase for each of a plurality of pixels of the first image, wherein each pixel corresponds to a particular point on the product, and wherein determining apparent magnification for each of a plurality of points on the product comprises determining apparent magnification at each of the plurality of points on the product based on the phase at the corresponding pixel.

7. The method of claim 1 further comprising determining focal length for each of the plurality of points on the product.

8. The method of claim 1 further comprising determining lens power for each of the plurality of points on the product.

9. The method of claim 1 further comprising determining standardized apparent magnification for each of the plurality of points on the product.

10. The method of claim 1 further comprising determining maximum apparent magnification and minimum apparent magnification for each of the plurality of points on the product.

11. The method of claim 10 further comprising determining a cylinder angle for each of the plurality of points on the product.

12. The method of claim 1 further comprising determining vertical disparity for each of the plurality of points on the product.

13. A method of determining optical quality of a transparent product, the method comprising:

projecting a sequence of phase-shifted sinusoidal gratings onto a reference plane;

obtaining an image with an image pickup device of each of the gratings within the sequence as seen through the product;

determining a phase for each of a plurality of pixels on the images, wherein each pixel corresponds to a particular point on the product; and determining optical quality at each of a plurality of points on the product based on the phase at the corresponding pixel.

14. The method of claim 13 wherein determining optical quality of the product comprises determining apparent magnification for each of the plurality of points on the product.

15. A method of determining optical quality of a transparent product, the method comprising:

positioning the product relative to an image generating device and an image pickup device such that light passing between the image generating device and the image pickup device passes through the product;

generating a sawtooth grating with the image generating device;

obtaining a first image of the sawtooth grating with the image pickup device, wherein the first image is influenced by the product;

generating a uniformly white target with the image generating device;

obtaining a second image of the uniformly white target with the image pickup device, wherein the second image is influenced by the product;

generating a uniformly dark target with the image generating device;

obtaining a third image of the uniformly dark target with the image pickup device, wherein the third image is influenced by the product;

determining a phase for each of a plurality of pixels on the images, wherein each pixel corresponds to a particular point on the product; and determining an optical characteristic for each of a plurality of points on the product based on the phase at the corresponding pixel.

16. The method of claim 15 wherein determining an optical characteristic for each of a plurality of points on the product comprises determining apparent magnification for each of the plurality of points.

17. An apparatus for determining optical quality of a transparent product, the apparatus comprising:

an image generating device for generating a gray-scale pattern;

an image pickup device for obtaining an image of the gray-scale pattern after the pattern has passed through the product; and an image analyzing device in communication with the image pickup device, the image analyzing device including instructions for determining apparent magnification for each of a plurality of points on the product based on the image.

18. A method of determining optical quality of a transparent product, the method comprising:

passing a sequence of phase-shifted periodic gray-scale patterns through the product;

obtaining an image with an image pickup device of each pattern within the sequence after each pattern has passed through the product;

determining a phase for each of a plurality of pixels on the images, wherein each pixel corresponds to a particular point on the product; and determining optical quality at each of a plurality of points on the product based on the phase at the corresponding pixel.

19. The method of claim 18 wherein determining optical quality of the product comprises determining apparent magnification for each of the plurality of points on the product.

20. The method of claim 18 wherein determining optical quality of the product comprises determining focal length for each of the plurality of points on the product.

21. The method of claim 18 wherein determining optical quality of the product comprises determining lens power for each of the plurality of points on the product.

22. The method of claim 18 wherein determining optical quality of the product comprises determining standardized apparent magnification for each of the plurality of points on the product.

23. The method of claim 18 wherein determining optical quality of the product comprises determining maximum apparent magnification and minimum apparent magnification for each of the plurality of points on the product.

24. The method of claim 23 wherein determining optical quality of the product comprises determining a cylinder angle for each of the plurality of points on the product.

25. The method of claim 18 wherein determining optical quality of the product comprises determining vertical disparity for each of the plurality of points on the product.

* * * * *